(12) United States Patent
Edmonson et al.

(10) Patent No.: US 7,650,788 B2
(45) Date of Patent: Jan. 26, 2010

(54) DIFFERENTIATION AND IDENTIFICATION OF ANALOGOUS CHEMICAL OR BIOLOGICAL SUBSTANCES WITH BIOSENSORS

(76) Inventors: Peter J. Edmonson, 138 Stone Church Road East, Hamilton, Ontario (CA) L9B 1A9; William D. Hunt, 109 Kirk Crossing Dr., Decatur, GA (US) 30030

( * ) Notice: Subject to any disclaimer, the term of this patent is extended or adjusted under 35 U.S.C. 154(b) by 96 days.

(21) Appl. No.: 11/976,345

(22) Filed: Oct. 24, 2007

(65) Prior Publication Data

US 2008/0127729 A1 Jun. 5, 2008

Related U.S. Application Data

(63) Continuation-in-part of application No. 11/088,809, filed on Mar. 25, 2005, now Pat. No. 7,451,649.

(51) Int. Cl.
*G01H 3/12* (2006.01)
(52) U.S. Cl. ...................................................... 73/599
(58) Field of Classification Search .................. 73/599, 73/584; 310/313 D
See application file for complete search history.

(56) References Cited

U.S. PATENT DOCUMENTS 4,361,026 A * 11/1982 Muller et al. ............... 73/24.01
5,571,568 A * 11/1996 Ribi et al. .................... 427/487
7,451,649 B2 * 11/2008 Edmonson et al. ............ 73/599

\* cited by examiner

*Primary Examiner*—Hezron Williams
*Assistant Examiner*—Tamiko D Bellamy
(74) *Attorney, Agent, or Firm*—Steven M. Greenberg, Esq.; Carey Rodriguez Greenberg & Paul LLP

(57) ABSTRACT

An RFID biosensor detection system for detecting particular substances has an interrogator circuit to transmit a radio frequency signal, an input transducer mounted on a piezoelectric material to receive an input radio frequency signal and propagate a corresponding acoustic wave within the piezoelectric material. At least two chemically orthogonal or semi-orthogonal biolayers are mounted on the piezoelectric material to receive substances to be tested and cause corresponding changes in the acoustic wave. An output transducer is mounted on the piezoelectric material to receive the acoustic wave and transmit a corresponding output radio frequency signal. A receiver circuit receives the corresponding output radio frequency signal and provides separate channel data indicative of the substances received.

16 Claims, 8 Drawing Sheets

A Multi-Dimensional RFID Biosensor And Processing System
100

Dual Track RFID Biosensor Configuration 200

(a)

RFID Biosensor Multiple Reflector Array Signals
500

(b)

RFID Biosensor Multiple Reflector Array Receiver
520

A 5-Bit Bi-Phase Barker Coded RFID/Biosensor With Multiple Biolayers 600

DIFFERENTIATION AND IDENTIFICATION OF ANALOGOUS CHEMICAL OR BIOLOGICAL SUBSTANCES WITH BIOSENSORS

RELATED APPLICATION

This application is a continuation-in-part of U.S. patent application Ser. No. 11/088,809 filed Mar. 25, 2005, the contents of which are hereby incorporated herein by reference.

FIELD OF THE INVENTION

This application relates to the differentiation and identification of analogous chemical and biological substances with RFID biosensors.

BACKGROUND OF THE INVENTION

Parent U.S. application Ser. No. 11/088,809 describes and claims a biosensor detection system for detecting a particular substance, said system having at least two biosensor devices, each biosensor device including a piezoelectric material, an input transducer mounted on the piezoelectric material to receive an input radio frequency signal and generate a corresponding acoustic wave within the piezoelectric material, an output transducer mounted on the piezoelectric material to receive the acoustic wave and transmit a corresponding output radio frequency signal, a biolayer mounted on the piezoelectric material to receive a substance to be tested and cause a corresponding change in the acoustic wave, and an oscillator circuit connected to the input transducer and to the output transducer, said oscillator circuit including an amplifier and providing an output signal indicative of a change in the acoustic wave, the biosensor devices having two different biolayers which are chemically orthogonal or semi-orthogonal to each other, whereby the output signals can be utilized to detect receipt of a particular substance by the biolayers of the biosensor devices.

SUMMARY OF THE INVENTION

The present invention provides acoustic wave (AW) radio frequency identification device (RFID) biosensors configured with chemically orthogonal or semi-orthogonal biolayers and a processing system which are capable of detecting differentiating and identifying analogous chemical and biological substances.

According to one aspect of the invention, an RFID biosensor detection system for detecting particular substances has an interrogator circuit to transmit a radio frequency signal, a piezoelectric material, an input transducer mounted on the piezoelectric material to receive an input radio frequency signal and propagate a corresponding acoustic wave within the piezoelectric material, at least two chemically orthogonal or semi-orthogonal biolayers mounted on the piezoelectric material to receive substances to be tested and cause corresponding changes in the acoustic wave an output transducer mounted on the piezoelectric material to receive the acoustic wave and transmit a corresponding output radio frequency signal, and a receiver circuit to receive the corresponding output radio frequency signal and provide separate channel data indicative of the substances received.

Classification of similar molecules in accordance with the present invention is based on the concept of the RFID biosensor having both the ability to detect using multiple chemically orthogonal or semi-orthogonal biolayers and to return back to a processing system an interrogation signal which has been suitably modified to contain multi-dimensional information. The processing system can then separate out the return signal and process the information to provide a multi-dimensional state-space map.

DESCRIPTION OF THE DRAWINGS

Embodiments of the invention will now be described, by way of example, with reference to the accompanying drawings, of which.

DESCRIPTION OF PREFERRED EMBODIMENTS

Figure 1:
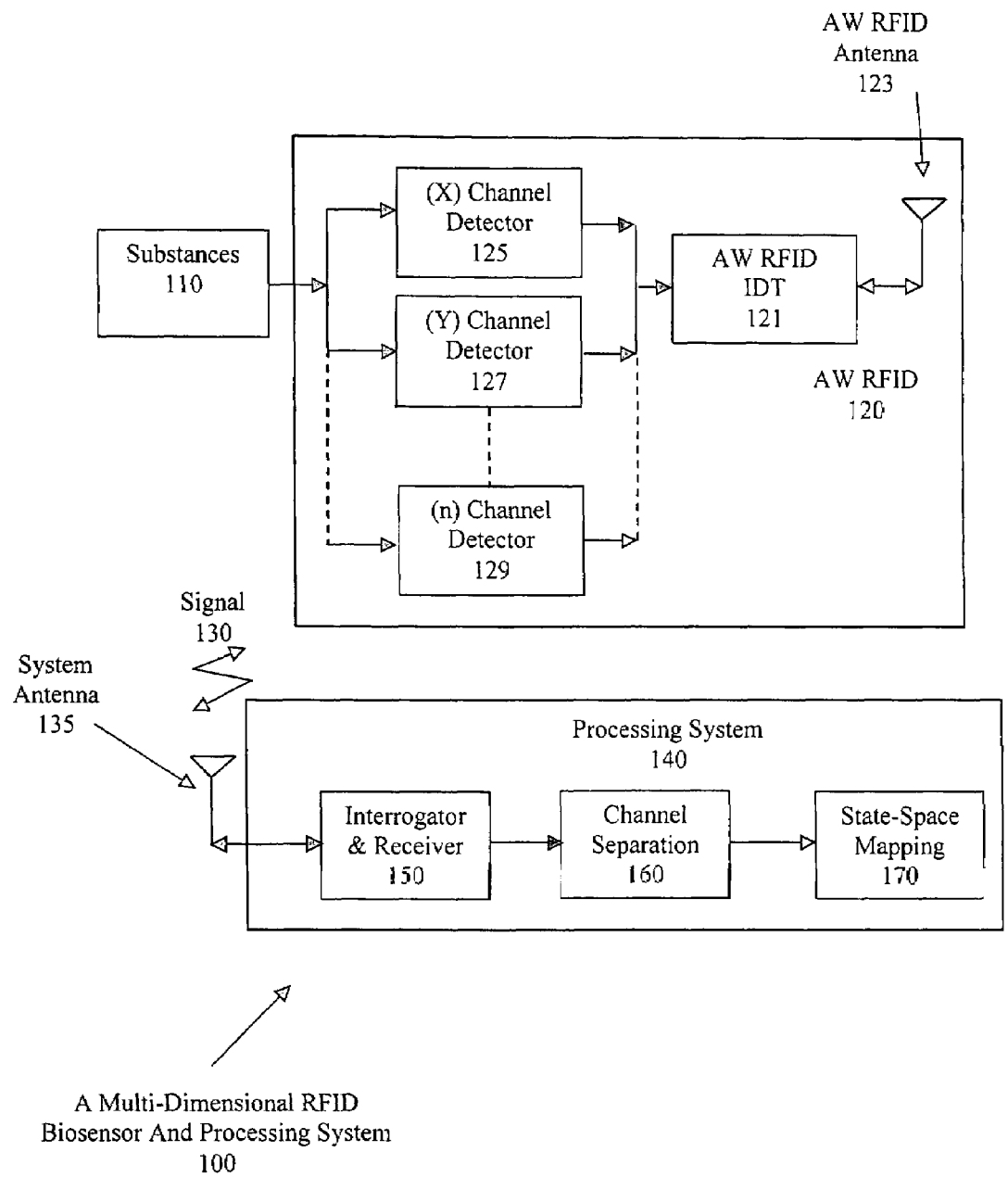
FIG. 1 is a diagrammatic view of a multi-dimensional RFID biosensor and processing system in accordance with one embodiment of the invention.

Referring to the drawings, a multi-dimensional RFID biosensor and processing system 100 is shown in FIG. 1. A quantity of substances 110 is presented to an AW RFID 120 which has a suitable AW RFID antennal 123 attached to an AW RFID inter-digital transducer (IDT) 121. The purpose of the AW RFID antenna 123 is to interface electromagnetic waves propagating in free space with the AW RFID IDT 121. The purpose of the AW RFID IDT 121 is to convert a received electrical signal 130 to acoustic waves and, similarly, convert acoustic waves to an electrical signal 130. Within the structure of the AW RFID 120, there are several chemically orthogonal or chemically semi-orthogonal receptor areas to detect certain substances 110 specific to each of the receptor regions. The first receptor region is configured at an (X) channel detector 125, the second receptor region is configured as (Y) channel detector 127 and continuing up to and including the ($n^{th}$) receptor region which is configured as the (n) channel detector 129. Each channel detector 125, 127 and continuing up to and including the (n) channel detector 129 is structured such that each channel detector is chemically orthogonal or chemically semi-orthogonal to each of the other channel detectors.

The sequence of detection for the multi-dimensional RFID biosensor and processing system 100 begins when a processing system 140 initiates, via an interrogator and receiver system 150, a signal 130 of suitable strength via an antenna 135 to stimulate the AW RFID 120. The electrical signal 130 is conveyed via the AW RFID antenna 123 to the AW RFID IDT 121 and converted to appropriate acoustic waves. The acoustic waves interact with the (X) channel detector 125, the (Y) channel detector 127 and continuing up to and including the (n) channel detector 129. The acoustic waves are modified only if the (X) channel detector 125 has detected any analogous (X) substances or, similarly, if the (Y) channel detector 127 has detected any analogous (Y) substances, and, similarly, if a channel detector continuing up to and including the (n) channel detector 129 has detected any analogous substances. The acoustic waves will be modified in accordance with the following equation (1) which was published in W. D. Hunt et al., "Time-dependent signatures of acoustic wave biosensors," IEEE Proceedings, Vol. 91, no. 6, pp. 890-901, June 2003;

$$\Delta f = -\frac{2f_u^2 h_f}{\sqrt{\rho_q \mu_q}}\left[\Delta \rho - \frac{\Delta \mu}{V_s^2}\right] \quad (1)$$

where $V_s$ is the acoustic velocity, $\rho$ is the density of the film, $h_f$ is the thickness of the film, $\mu_q$ and $\rho_q$ are the shear stiffness and density of the quartz crystal respectively, $\mu$ is the stiffness of the film, and $\Delta$ is the difference between perturbed and unperturbed (denoted by subscript u) quantities. The stiffness of the film, $\mu$, is affected by the conformational change of the recognition molecules.

The result is that the AW RFID 120 now has generated acoustic waves with detection information pertaining to the (X) channel detector 125, the (Y) channel detector 127 and continuing up to and including the (n) channel detector 129. The AW RFID IDT 121 now combines and converts these acoustic waves to electrical signals which are conveyed via the AW RFID antenna 123 as a signal 130 returning to the processing system 140 and into the interrogator and receiver 150 via a system antenna 135. The interrogator and receiver 150 receive these modified signals and processes them within a channel separation step 160 where the combined detection information from each of the (X) channel detector 125, the (Y) channel detector 127 and continuing up to and including the (n) channel detector 129 is separated out and stored within a (X) location, a (Y) location and continuing up to and including the ($n^{th}$) location. Finally, the data from these stored locations is mapped using state-space mapping 170. The final result is that each detected analogous substance is projected onto a multi-dimensional state-space map.

The main advantages of detecting, differentiating and identifying analogous chemical and biological substances using RFID biosensor type devices in accordance with the present invention:

(1) encompassing n-chemically orthogonal or semi-orthogonal biolayers within the RFID biosensor structure,
(2) the returned interrogation signal has the means and capacity to contain the detected information from the n-biolayers,
(3) the receiver within the interrogation system can then separate out the n-orthogonal or semi-orthogonal channels and process the information to complete an n-dimensional state-space map.

Various RFID biosensor structures in accordance with the invention can be fashioned to incorporate multiple chemically orthogonal or semi-orthogonal biolayers and produce signals which have the means and capacity to contain detected data from the multiple chemically orthogonal or semi-orthogonal biolayers, as will now be described. Receiver structures will also be described to illustrate how data from each channel can be separated out to distinguish X, Y and up to n data sets to formulate a multi-dimensional state-space map.

Dual Track RFID Biosensor

Figure 2:
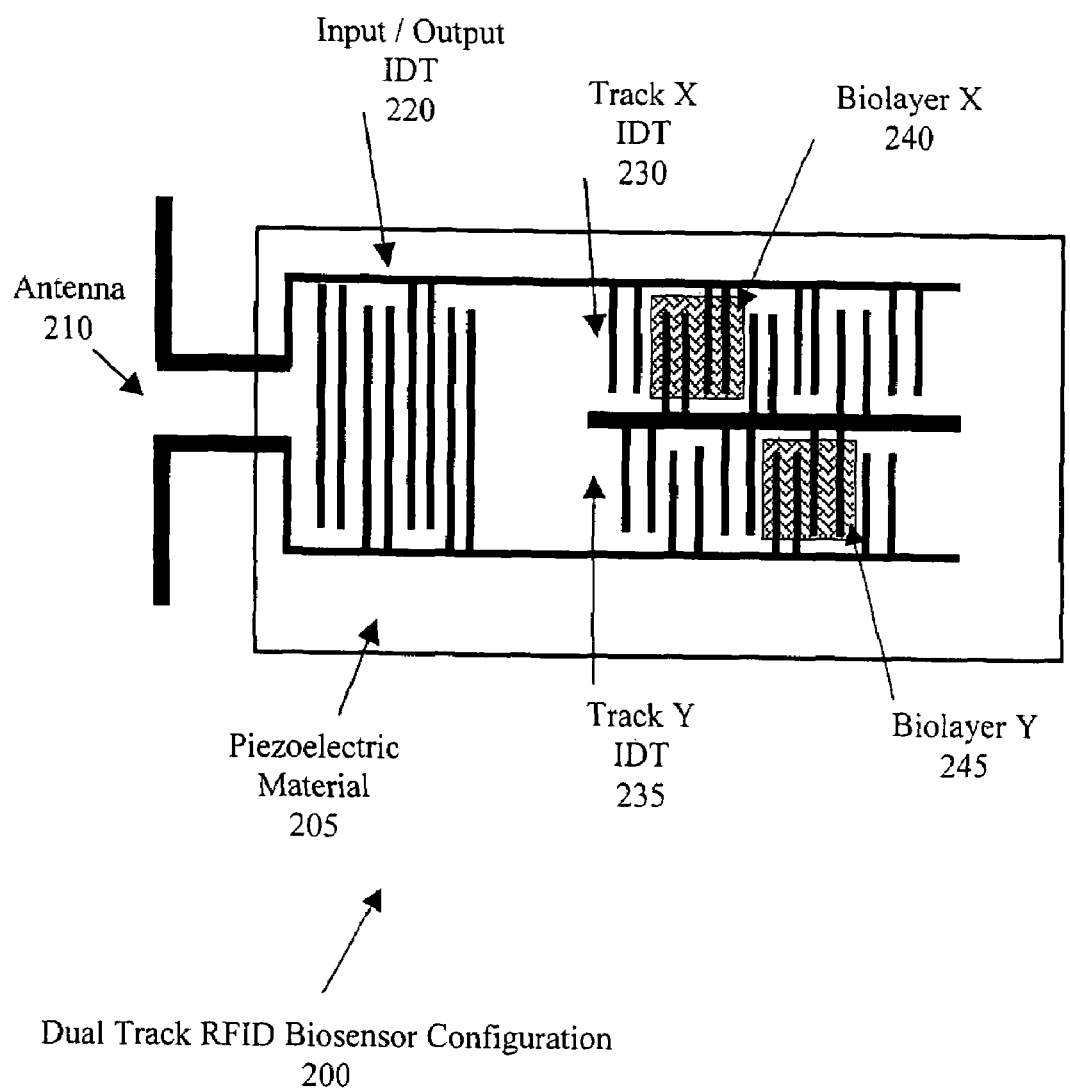
FIG. 2 shows a dual track RFID biosensor configuration.

A schematic view of a dual track RFID biosensor configuration 200 is shown in FIG. 2. This concept is an extension of the DUAL TRACK SURFACE ACOUSTIC WAVE RIFD/SENSOR described in U.S. Pat. No. 7,005,964 (Edmonson et al.) issued Feb. 28, 2006. An interrogation signal interacts with an antenna 210 which is electrically connected to an input/output IDT 220. A piezoelectric material 205 enables electrical signals within the input/out IDT 220 to be converted to acoustic waves. The antenna 210 is also electrically connected to track X IDT 230 and to track Y IDT 235 where similar interactions also convert electrical signals to acoustic waves. A chemically orthogonal or semi-orthogonal biolayer X 240 is suitably positioned within track X IDT 230 such that, if substances which are analogous to biolayer X 240 reach receptor sites within the biolayer X 240, a perturbation of the acoustic waves as specific to those which interact with track X IDT 230 and the input/output IDT 220 will cause a modification of the returned interrogation signal, when the acoustic waves transform the perturbations into electrical signals via the input/output IDT 220 and track X IDT 230. Similarly, a chemically orthogonal or semi-orthogonal biolayer Y 245 is suitably positioned within the track Y IDT 235 such that, if substances which are analogous to biolayer Y 245 reach receptor sites within the biolayer Y 245, a perturbation of the acoustic waves specific to those which interact with track Y IDT 235 and the input/output IDT 220 will cause a modification of the returned interrogation signal, when the acoustic waves transform the perturbations into electrical signals via the input/output IDT 220 and the track Y IDT 235.

The dual track RFID biosensor configuration 200 is shown with a split finger design, with both the width and spacing of the fingers being one-eighth of an acoustic wavelength. The dual track RFID biosensor configuration 200 can equally function with a typical quarter-wavelength design where both the width and spacing of the fingers are one-quarter of an acoustic wavelength. The key to this dual track configuration is the phase of offset of 90° or one-quarter of an acoustic wavelength between the track X IDT 230 and the track Y IDT 235. This offset will produce a returned interrogation signal similar to the dual track RFID biosensor signal 300 shown in FIG. 3(a). Signal X 304 is a result of the acoustic waves propagating by way of the area within the track X IDT 230, and signal Y 308 is the result of the acoustic waves propagating by way of the area within the track Y IDT 235. Signal X 304 is 90° phase displaced with respect to signal Y 308.

Figure 3:
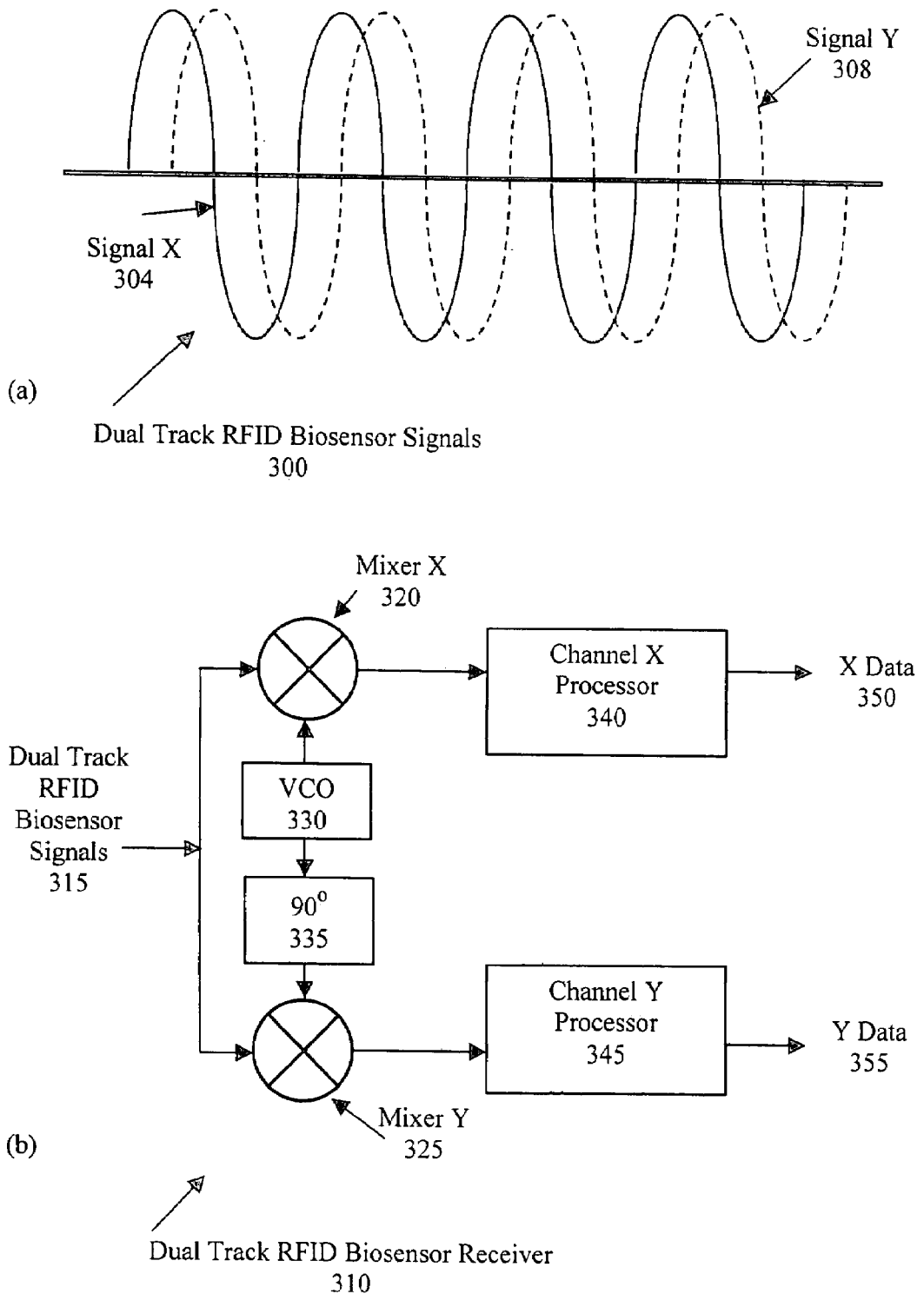
FIG. 3(a) shows the dual track RFID biosensor signals.
FIG. 3(b) shows a dual track RFID biosensor receiver.

The dual track RFID biosensor receiver 310 shown in FIG. 3(b) demodulates and separates out the independent data from biolayer X 240 and biolayer Y 245. The dual track RFID biosensor signals 315, which are electrically phase displaced by 90°, are split along two paths so that two equally divided signals by the inputs for both mixer X 320 and mixer Y 325. A voltage controlled oscillator (VCO) 330 signal is applied to down-convert within the mixer X 320 a signal which acts as the input to the channel X processor 340. The channel X processor 340 suitably converts the signals such that X data 350 is a function of the substances which are analogous to biolayer X 240. Similarly, for the Y data, the VCO 330 signal is electrically offset in phase by 90° by a phase shifter 335 as it is applied to down-convert within the mixer Y 325 a signal which acts as the input to the channel Y processor 345. The channel Y processor 345 suitably converts the signals such that Y data 355 is a function of the substances which are analogous to biolayer Y 245.

RFID Biosensor with Multiple Reflector Arrays

Figure 4:
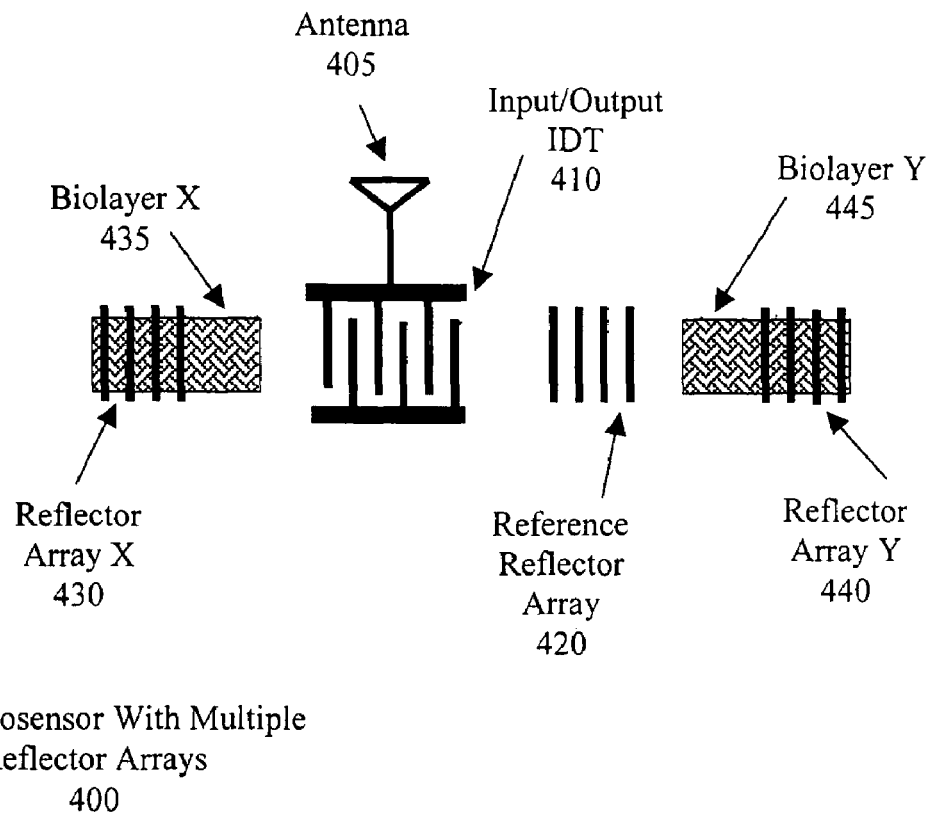
FIG. 4 shows an RFID biosensor with multiple reflector arrays.

FIG. 4 shows another configuration utilizing AW RFID biosensors in accordance with the invention. An RFID biosensor 400 with multiple reflector arrays is used to embed the multiple biolayer information with any time-displaced signal. This concent is an extension of the concept disclosed in U.S. Pat. No. 7,053,524 (Edmonson et al.) issued May 30, 2006. An antenna 405 is electrically connected to an input/output IDT 410, and an interrogation signal entering the antenna 405 is converted via the input/output IDT 410 to acoustic waves propagating outwards from both sides of the input/output IDT 410. The acoustic waves intercept a reference reflector array 420, a reflector array X 430 and a reflector array Y 440. Other arrays can also be included, up to the $n^{th}$ reflector array. The action of the reflector arrays 420, 430 and 440 is such that an incident acoustic wave will partially transmit through, but more importantly, partially reflect back towards the input/output IDT 410. The reference reflector array 420 has no biolayer placed within its proximity and will reflect back an acoustic wave of similar characteristics to that of the incident propagating acoustic wave.

Reflector array X 430 has in its proximity a chemically orthogonal or semi-orthogonal biolayer X 435 where, if substances which are analogous to biolayer X 435 reach the receptor sites within biolayer X 435, a perturbation of the acoustic waves specific to those which interact with reflector array X 430 will cause a modification of the characteristics of the reflected acoustic wave being propagated back to the input/output IDT 410. Similarly, reflector array Y 440 has in its proximity a chemically orthogonal or semi-orthogonal biolayer Y 445 where, if substances which are analogous to biolayer Y 445 reach the receptor sites within biolayer Y 445, a perturbation of the acoustic waves specific to those which interact with reflector Y 440 will cause a modification of the characteristics of the reflected acoustic wave being propagated back to the input/output IDT 410. These collections of reflected acoustic waves from reflector arrays 420, 430 and 440 converge at separate times at the input/output IDT 410 and are converted to equivalent electrical signals which propagate back to the processing system 140 via the antenna 405.

Figure 5:
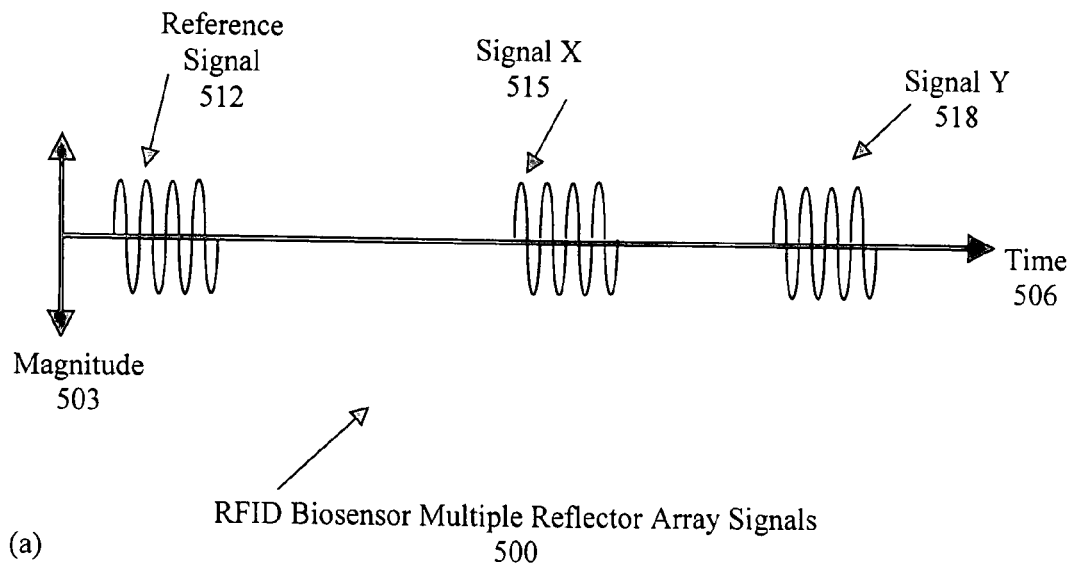
FIG. 5(a) shows RFID biosensor and multiple reflector array signals.
FIG. 5(b) shows an RFID biosensor and multiple reflector array receiver.
Figure 5:
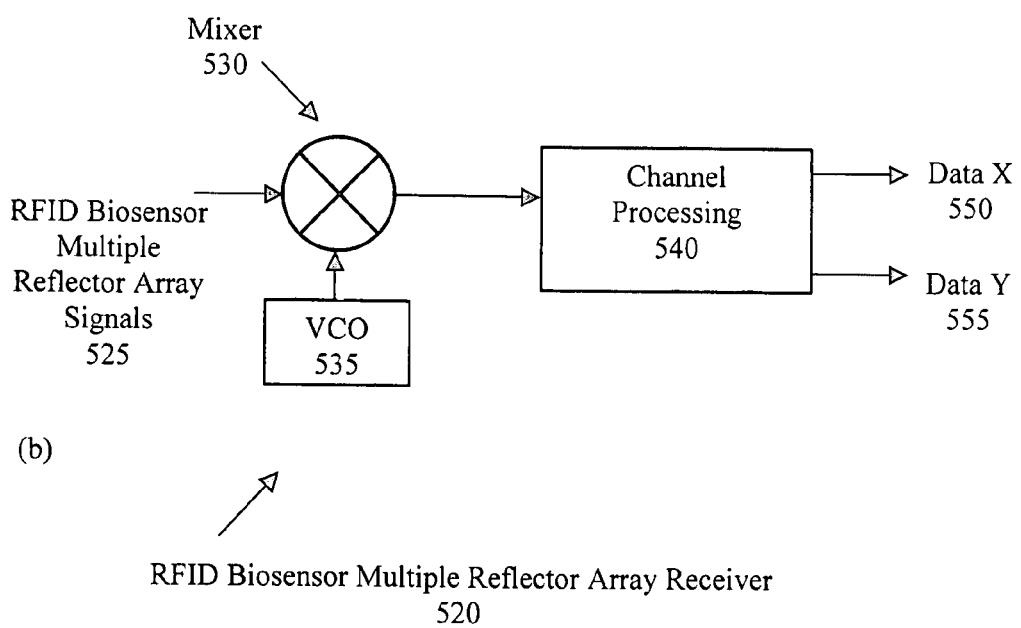

Such RFID biosensors with multiple reflector array signals 500 are shown in FIG. 5(a) where the axes are magnitude 503 and time 506. A reference signal 512 is the first signal to be returned back to the interrogation system, because normal positioning of the reference reflector array 420 dictates that it be located geometrically closest to the input/output IDT 410. Signal X 515 is separate in time and will be distinct in characteristics from both the reference signal 512 and signal Y 518 if substances which are analogous to biolayer X 435 reach the receptor sites within biolayer X 435. Similarly, signal Y 518 is separate in time and will be distinct in characteristics from both the reference signal 512 and signal X 515 if substances which are analogous to biolayer Y 445 reach the receptor sites within biolayer Y 445. The time separation between the electrical signals 512, 515 and 518 is a function of the spatial layout of the reference reflector array 420, reflector array X 430 and reflector array Y 440. A person skilled in the art will take care in positioning the input/output IDT 410, the reference reflector 420, reflector array X 430 and reflector array Y 440 and any other reflector arrays so as not to cause interference within the RFID biosensor with multiple reflector array signals 500 (FIG. 5(a)). A person skilled in the art will also take advantage of the multiple reflections which occur in time after signal Y 518 due to the multiplicity of reflections which occur in the acoustic wave path between reflector array X 430 and reflector array Y 440.

An RFID biosensor multiple reflector array receiver 520 is shown in FIG. 5(b). RFID biosensor multiple reflector array signals 525 are the input to a mixer 530 along with a VCO 535 signal to produce a down-converted signal for channel processing 540. The channel processing 540 uses the reference signal 512 to null out any irregularities due to temperature and other physical changes and separate out data signals such that data X 550 is a function of the substances which are analogous to biolayer X 435 and such that data Y 555 is a function of the substances which are analogous to biolayer Y 445.

The RFID biosensor with multiple reflector arrays 400, the RFID biosensor with multiple reflector array signals 500 and the RFID biosensor with multiple reflector array receiver 520 can be extended to an n-dimensional system capable of producing n-dimensional state-space mapping for analogous substances, as will now be readily apparent to a person skilled in the art.

RFID Biosensors With Correlation Based Detection Schemes

A useful feature which is inherent in AW RFID biosensors is the ability to encode the interdigital transducers such that the encoding process of the AW RFID device expands the data over a specific frequency range and that, within the receiver, a reference compressor then correlates the data to produce a correlation function which is time based and convenient for extraction of certain information. Any deviation of the signals within the AW RFID biosensor expander will then alter the peak and sidelobes of the final correlation function when using a reference compressor which remains constant. These encoding methods have previously been described in U.S. Pat. No. 7,053,524 (Edmonson et al.) issued May 30, 2006, with a more detailed description of the correlation functions being found in P. J. Edmonson, "SAW pulse compression using combined Barker codes, Masters Thesis in Electrical Engineering, McMaster University, Hamilton, Ontario, 124 pages, March 1989.

Figure 6:
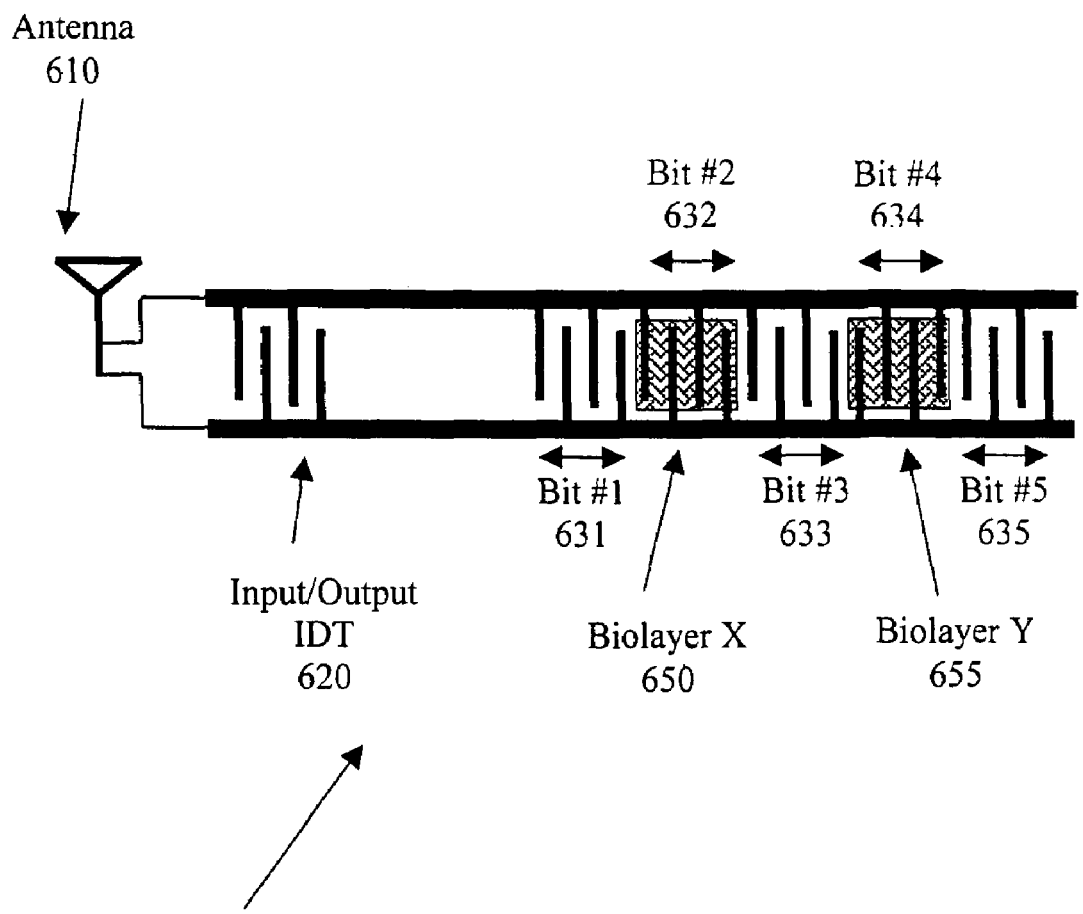
FIG. 6 shows basic elements and structure of a wireless five-bit bi-phase Barker coded RFID biosensor with multiple biolayers.

A 5-bit bi-phase Barker coded RFID biosensor with multiple chemically orthogonal or semi-orthogonal biolayers 600 is shown in FIG. 6. Initially, an antenna 610 accepts an interrogation signal from a processing system 140 (FIG. 1) located some distance away. This signal is converted to an acoustic wave via an input/output interdigital transducer IDT 620 and progresses towards the coded IDT section constituting Bit #1 631, Bit #2 632, Bit #3 633, Bit #4 634 and Bit #5 635. Similarly, the signal from the antenna 610 is also electrically connected to the coded IDT section constituting Bit #1 631, Bit #2 632, Bit #3 633, Bit #4 634 and Bit #5 635 to generate another acoustic wave which progresses towards the input/output IDT 620. These acoustic waves interact with the multiple IDTs 620, 631, 632, 633, 634 and 635 to convert the acoustic waves back to a coded electrical system which is transmitted back out from the antenna 610 to the processing system 140.

The geometric positioning of the fingers, which dictates the polarity of the IDTs is important for bi-phase coded structures. In this embodiment, each bit is made up of two finger pairs, with each finger pair being made up of oppositely positioned fingers. The finger pairs are continuous for Bit #1 631, Bit #2 632 and Bit #3 633 but are interchanged during the transition from Bit #3 633 to Bit #4 634 and during the transition from Bit #4 634 to Bit #5 635. This sequence of finger geometry now represents the 5-bit bi-phase Barker code of 1, 1, 1, −1, 1 where there is a 180° phase transition between the third and fourth and fourth and fifth bits. Also, in this embodiment, chemically orthogonal or semi-orthogonal biolayer X 650 is positioned within the finger structure of Bit

2 632, and chemically orthogonal or semi-orthogonal biolayer Y 655 is positioned within the finger structure of Bit #4 634.

The correlation function can be derived by using signal processing techniques on the coded electrical signal which is transmitted back out from the antenna 610 to the processing system 140. This signal processing technique comprises a series of time inversion multiplications, shifting and summing between the returned coded signal (expander) and a reference code (compressor). The following Table 1 illustrates this correlation process for a 5-bit bi-phase Barker code of sequence (1, 1, 1, −1, 1).

TABLE 1

| Row # | | | | | | | | | |
|---|---|---|---|---|---|---|---|---|---|
| 1 | 1 | −1 | 1 | 1 | 1 | | | | |
| 2 | | 1 | −1 | 1 | 1 | 1 | | | |
| 3 | | | 1 | −1 | 1 | 1 | 1 | | |
| 4 | | | | −1 | 1 | −1 | −1 | −1 | |
| 5 | | | | | 1 | −1 | 1 | 1 | 1 |
| 6 | | | | | | | | | |
| 7 | 1 | 0 | 1 | 0 | 5 | 0 | 1 | 0 | 1 |

In row #1, the time reversed code is placed within each bit being multiplied by the first bit of the Barker sequence, which in this example is a "1". Similarly, in row #2, the time reversed code is shifted by one bit period and multiplied by the second bit of the Barker sequence, which in this example is a "1". For row #3, the time reversed code is again shifted by one bit period and multiplied by the third bit of the Barker sequence, which in this example is a "1". For row #4, the time reversed code is again shifted by one bit period and multiplied by the fourth bit of the Barker sequence, which in this example is a "−1" and for row #5, the time reversed code is again shifted by one bit period and multiplied by the fifth bit of the Barker sequence, which in this example is a "1". Row #7 is the sum of the bits positioned in the columns directly above each value. The resulting correlation function is then, 1, 0, 1, 0, 5, 0, 1, 0, 1.

Perturbations within the area of the biolayers will change the correlation function. The changes are both distinguishable and distinct to each separately placed biolayer. Such perturbations are caused due to substances which are analogous to biolayer X 650 interacting with the receptor sites within biolayer X 650 to produce a perturbation of the acoustic waves specific to those which interact with bit #2 632. Similarly, perturbations which are caused due to substances that are analogous to biolayer Y 655 interacting with the receptor sites within biolayer Y 655 produce a perturbation of the acoustic waves specific to those which interact with bit #4 634.

The following Table 2 illustrates a correlation process for a 5-bit bi-phase Barker code of sequence (1, 0.75, 1, −1, 1) when the second bit is first perturbed, for this embodiment from a value of "1" to a value of "0.75". This perturbation would be the result of a change within the biolayer X 650 which is positioned in proximity to Bit #2 632.

TABLE 2

| Row # | | | | | | | | | |
|---|---|---|---|---|---|---|---|---|---|
| 1 | 1 | −1 | 1 | 0.75 | 1 | | | | |
| 2 | | 1 | −1 | 1 | 0.75 | 1 | | | |
| 3 | | | 1 | −1 | 1 | 0.75 | 1 | | |
| 4 | | | | −1 | 1 | −1 | −0.75 | −1 | |
| 5 | | | | | 1 | −1 | 1 | 0.75 | 1 |

TABLE 2-continued

| Row # | | | | | | | | | |
|---|---|---|---|---|---|---|---|---|---|
| 6 | | | | | | | | | |
| 7 | 1 | 0 | 1 | −0.25 | 4.75 | −0.25 | 1.25 | −0.25 | 1 |

One of the distinct features of this perturbed correlation function is that the changes occur near the middle and to the right hand side of the correlation function.

The following Table 3 illustrates a correlation process for a 5-bit bi-phase Barker code of sequence (1, 1, 1, −0.75, 1) when the fourth bit is perturbed, in this example from a value of "−1" to a value of "−0.75". This perturbation would be the result of a change within the biolayer Y 655 which is positioned in proximity to Bit #4 634.

TABLE 3

| Row # | | | | | | | | | |
|---|---|---|---|---|---|---|---|---|---|
| 1 | 1 | −0.75 | 1 | 1 | 1 | | | | |
| 2 | | 1 | −0.75 | 1 | 1 | 1 | | | |
| 3 | | | 1 | −0.75 | 1 | 1 | 1 | | |
| 4 | | | | −1 | 0.75 | −1 | −1 | −1 | |
| 5 | | | | | 1 | −0.75 | 1 | 0.75 | 1 |
| 6 | | | | | | | | | |
| 7 | 1 | 0.25 | 1.25 | 0.25 | 4.75 | 0.25 | 1 | 0 | 1 |

One of the distinct features of Table 3 is that the perturbed correlation function changes occur near the middle and to the left hand side of the correlation function, which is opposite to that of Table 2.

Figure 7:
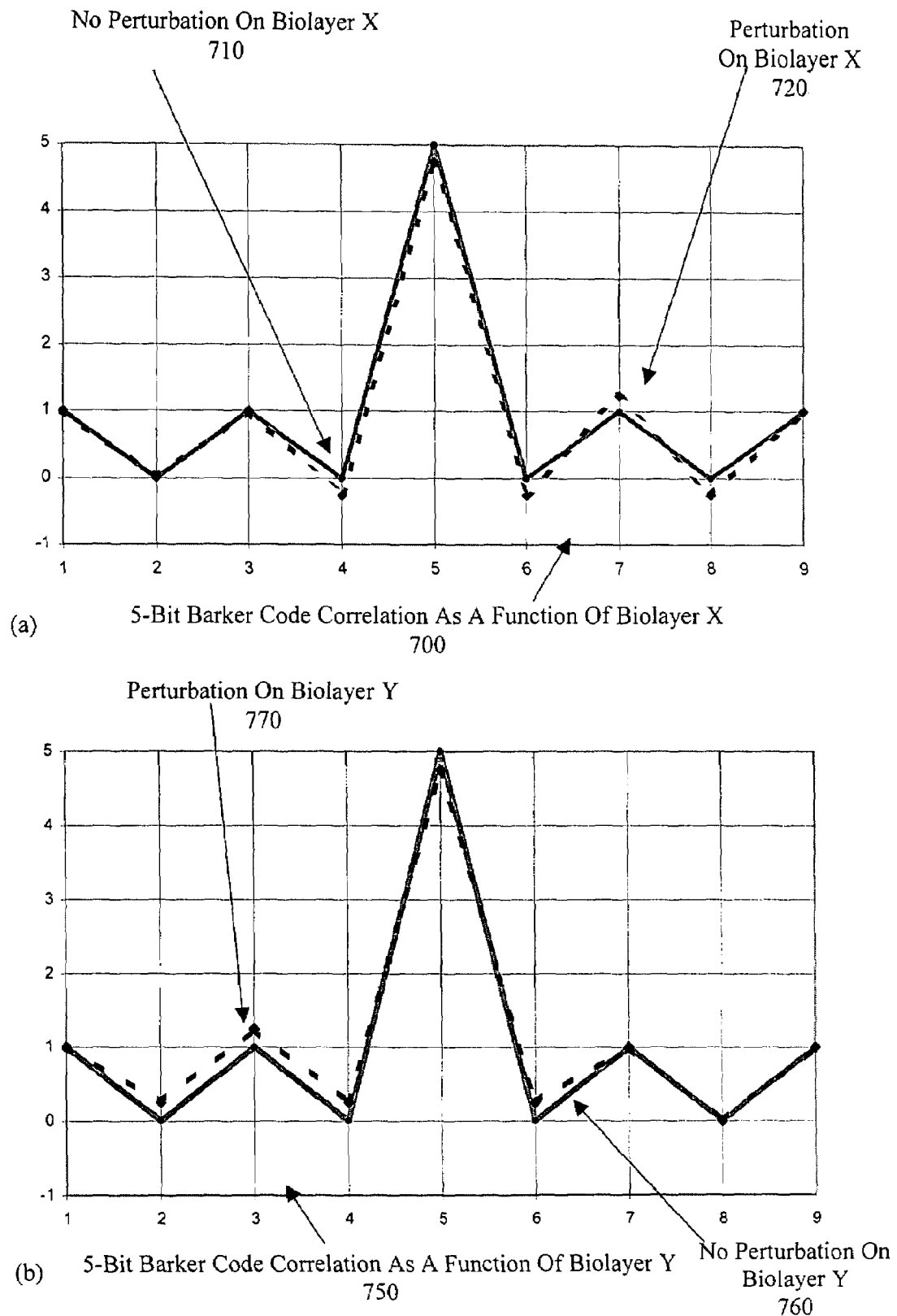
FIG. 7(a) is a graph showing a five-bit Barker code correlation as a function of biolayer X.
FIG. 7(b) is a graph showing a five-bit Barker code correlation as a function of biolayer Y.

A comparison of a 5-bit Barker code correlation as a function of biolayer X 700 is shown in FIG. 7(*a*). The graph outlining no perturbation on biolayer X 710 shows an unperturbed correlation function (solid line) as calculated from row 7 of Table 1, and a perturbed correlation function derived from a perturbation on biolayer X 720 (dashed line) as calculated from row 7 of Table 2. Similarly, a comparison of a 5-bit Barker code correlation as a function of biolayer Y 750 is shown in FIG. 7(*b*). The graph outlining no perturbation on biolayer Y 760 shows an unperturbed correlation function (solid line) as calculated from row 7 of Table 1, and a perturbed correlation function derived from a perturbation on biolayer Y 770 (dashed line) as calculated from row 7 of Table 3. Another distinct feature of the four correlation functions 710, 720, 760 and 770 is that the extreme sidelobes never change in value, allowing for a built-in amplitude reference to compare other peak and sidelobe amplitude changes with.

Figure 8:
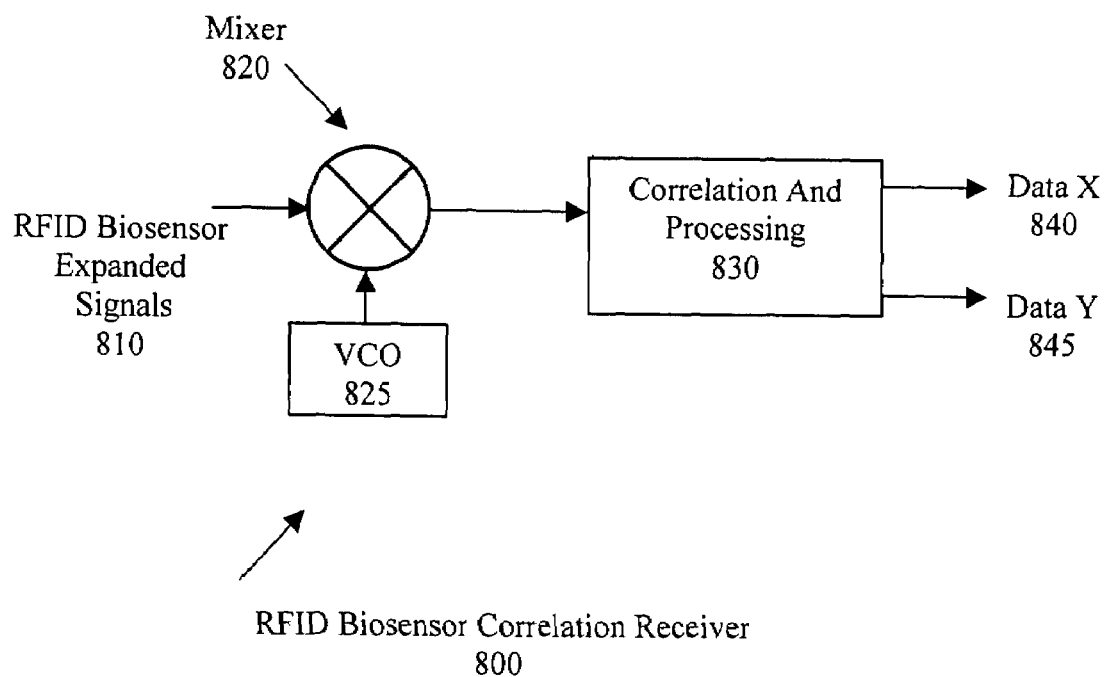
FIG. 8 shows an RFID biosensor correlation receiver.

An RFID biosensor correlation receiver 800 is shown in FIG. 8. A variety of RFID biosensor expanded signals 810 are inputted to a mixer 820 and, with the use of the VCO 825, are down-converted for further correlation and processing 830. The correlation and processing 830 separates out data signals depending upon the encoding used, such that data X 840 is a function of the substances which are analogous to biolayer X 650 and data Y 845 is a function of the substances which are analogous to biolayer Y 655.

The above example describing a 5-bit bi-phase Barker coded RFID biosensor with multiple chemically orthogonal or semi-orthogonal biolayers 600, the correlation as a function of biolayer X 700, the correlation as a function of biolayer Y 750 and an RFID biosensor correlation receiver 800 can be extended by those skilled in the art to an n-dimensional chemically orthogonal or semi-orthogonal system capable of producing n-dimensional state-space mapping.

The previously described three methods of utilizing AW RFID biosensors to detect, differentiate and identify analogous chemical and biological substances are not limited to only the two-dimensional X and Y data for the construction of a state-space map, but can be expanded by those skilled in the art to n-dimensional configurations. One technique to include several chemically orthogonal and semi-orthogonal biolayers would be to combine the structures of the dual track RFID biosensor configuration 200 (FIG. 2) with that of the RFID biosensor with multiple reflector arrays 400 (FIG. 4). Expansion of the 5-bit bi-phase Barker coded RFID biosensor with multiple biolayers 600 may include but not be limited to the use of other Barker codes such as the 13 bit Barker code and combined Barker codes, pseudorandom (PN) codes, linear frequency modulation (FM) codes, non-linear FM codes and Frank codes.

Other embodiments and advantages of the invention will now be readily apparent to a person skilled in the art, the scope of the invention being defined in the appended claims.

What is claimed is:

1. An RFID biosensor detection system for detecting particular substances, said system having:
   an interrogator circuit to transmit a radio frequency signal;
   a piezoelectric material;
   an input transducer mounted on the piezoelectric material to receive an input radio frequency signal and propagate a corresponding acoustic wave within the piezoelectric material;
   at least two chemically orthogonal or semi-orthogonal biolayers mounted on the piezoelectric material to receive substances to be tested and cause corresponding changes in the acoustic wave;
   an output transducer mounted on the piezoelectric material to receive the acoustic wave and transmit a corresponding output radio frequency signal;
   a receiver circuit to receive the corresponding output radio frequency signal and provide separate channel data indicative of the substances received; and
   a processing system to initiate an interrogation procedure.

2. An RFID biosensor detection system according to claim 1 wherein the processing system effects channel separation of data using correlation functions.

3. An RFID biosensor detection system according to claim 1 wherein the processing system has a state-space map formulator operable to produce a signal state-space map from the separate channel data whereby receipt of the particular substances by the biolayers of the RFID biosensor can be detected.

4. An RFID biosensor detection system according to claim 1 wherein each transducer is an interdigital transducer.

5. An RFID biosensor detection system according to claim 1 wherein each biolayer is located on an interdigital transducer.

6. An RFID biosensor detection system according to claim 1 wherein an array of reflectors causes a corresponding change in the acoustic wave.

7. An RFID biosensor detection system according to claim 6 wherein each biolayer is located on a reflector.

8. An RFID biosensor detection system according to claim 1 wherein the biolayer of each RFID biosensor device comprises an antibody, which is chemically orthogonal or semi-orthogonal to an antibody of the other biolayer.

9. An RFID biosensor detection system for detecting particular substances, said system having:
   an interrogator circuit to transmit a radio frequency signal;
   a piezoelectric material;
   an input transducer mounted on the piezoelectric material to receive an input radio frequency signal and propagate a corresponding acoustic wave within the piezoelectric material;
   at least two chemically orthogonal or semi-orthogonal biolayers mounted on the piezoelectric material to receive substances to be tested and cause corresponding changes in the acoustic wave;
   an output transducer mounted on the piezoelectric material to receive the acoustic wave and transmit a corresponding output radio frequency signal;
   a receiver circuit to receive the corresponding output radio frequency signal and provide separate channel data indicative of the substances received; and
   a processing system to effect the channel separation of data using correlation functions.

10. An RFID biosensor detection system according to claim 9 wherein the processing system initiates an interrogation procedure.

11. An RFID biosensor detection system according to claim 9 wherein the processing system has a state-space map formulator operable to produce a signal state-space map from the separate channel data whereby receipt of the particular substances by the biolayers of the RFID biosensor can be detected.

12. An RFID biosensor detection system according to claim 9 wherein each transducer is an interdigital transducer.

13. An RFID biosensor detection system according to claim 9 wherein each biolayer is located on an interdigital transducer.

14. An RFID biosensor detection system according to claim 9 wherein an array of reflectors causes a corresponding change in the acoustic wave.

15. An RFID biosensor detection system according to claim 14 wherein each biolayer is located on a reflector.

16. An RFID biosensor detection system according to claim 9 wherein the biolayer of each RFID biosensor device comprises an antibody, which is chemically orthogonal or semi-orthogonal to an antibody of the other biolayer.

* * * * *